US006978167B2

(12) United States Patent
Dekel et al.

(10) Patent No.: US 6,978,167 B2
(45) Date of Patent: Dec. 20, 2005

(54) VIDEO POSE TRACKING SYSTEM AND METHOD

(75) Inventors: Doron Dekel, Toronto (CA); Claudio Gatti, Toronto (CA)

(73) Assignee: Claron Technology Inc., Toronto (CA)

(*) Notice: Subject to any disclaimer, the term of this patent is extended or adjusted under 35 U.S.C. 154(b) by 513 days.

(21) Appl. No.: 10/184,972

(22) Filed: Jul. 1, 2002

(65) Prior Publication Data

US 2004/0002642 A1   Jan. 1, 2004

(51) Int. Cl.[7] ............................................. A61B 5/05
(52) U.S. Cl. ..................... 600/426; 600/414; 356/620
(58) Field of Search .............................. 600/407, 426, 600/424, 410, 411, 437, 374, 512, 592, 417, 600/450, 558, 117, 454, 414, 441, 409, 508, 600/595; 382/103, 190, 195, 154, 206, 169, 382/173–4, 77, 203, 205–6, 131, 260, 299; 345/156; 606/130; 356/620

(56) References Cited

U.S. PATENT DOCUMENTS

| | | | | |
|---|---|---|---|---|
| 3,617,759 A | * | 11/1971 | Martin | ........................ 356/620 |
| 4,945,914 A | * | 8/1990 | Allen | .......................... 600/426 |
| 5,016,639 A | * | 5/1991 | Allen | .......................... 600/426 |
| 5,097,839 A | * | 3/1992 | Allen | .......................... 600/426 |
| 5,603,318 A | | 2/1997 | Heilbrun et al. | |
| 5,769,789 A | * | 6/1998 | Wang et al. | ................. 600/414 |
| 5,792,147 A | | 8/1998 | Evans et al. | |
| 5,823,958 A | * | 10/1998 | Truppe | .......................... 600/426 |
| 5,828,770 A | * | 10/1998 | Leis et al. | ................... 382/103 |
| 6,018,592 A | * | 1/2000 | Shinagawa et al. | .......... 382/195 |
| 6,072,903 A | * | 6/2000 | Maki et al. | .................. 382/190 |
| 6,351,659 B1 | | 2/2002 | Vilsmeier | |
| 6,351,661 B1 | | 2/2002 | Cosman | |
| 6,368,285 B1 | * | 4/2002 | Osadchy et al. | ............. 600/508 |
| 6,381,485 B1 | * | 4/2002 | Hunter et al. | ................ 600/407 |
| 6,490,475 B1 | * | 12/2002 | Seeley et al. | ................ 600/426 |
| 6,560,354 B1 | * | 5/2003 | Maurer et al. | ............... 600/424 |
| 6,801,637 B2 | * | 10/2004 | Voronka et al. | .............. 382/103 |

(Continued)

FOREIGN PATENT DOCUMENTS

| | | |
|---|---|---|
| EP | 0 501 993 | 6/1997 |
| GB | 2246261 | 1/1992 |
| WO | WO 01/19273 | 3/2001 |

OTHER PUBLICATIONS

T.A. Clarke, An Analysis of the Properties of Targets Used in Digital Close Range Photogrammetric Measurement, SPIE, vol. 2350, 1994, p. 251-262.

*Primary Examiner*—Brian L. Casler
*Assistant Examiner*—Baisakhi Roy
(74) *Attorney, Agent, or Firm*—Bereskin & Parr

(57) ABSTRACT

A measurement system and method for detecting and tracking the pose of an object displaceable in a coordinate reference frame. In the system and method a visible target pattern is provided on the object. The visible target pattern includes a series of contrast regions for providing at least two feature points. Each of these feature points is located at a juncture of an optically detectable plurality of edges. Each edge in the optically detectable plurality of edges separates different contrast regions. The method and system determine the location of the feature points by first locating the edges using the change in contrast between contrast regions, and then determining junctures of multiple edges. The method and system also involve a stereoscopic digital camera for generating a pair of digital images of the target pattern and a marker template comprising a set of reference characteristics including a relationship between the feature points.

37 Claims, 11 Drawing Sheets

U.S. PATENT DOCUMENTS

2001/0024512 A1  9/2001  Yoronka et al.
2004/0070565 A1 *  4/2004  Nayar et al. ................ 345/156

* cited by examiner

VIDEO POSE TRACKING SYSTEM AND METHOD

The present invention relates to the computerized optical measurement of the position and orientation of objects in space.

BACKGROUND OF THE INVENTION

There is a great interest in surgical and other arenas to provide for the real-time computerized measurement of a spatial position and orientation (pose) of specially marked objects moving unpredictably through an unstructured scene. For one example application, the scene may be an operating room in which surgery is performed, and the tracked objects are surgical instruments, and implants to be secured to the patient's anatomy in pre-planned positions. The pose of the surgical instruments is monitored by position sensors, such that the real-time location of the instruments can be displayed on previously acquired patient image data. The pose of the patient is also typically tracked separately, to allow for sensing of anatomy movement relative to the tracked instruments during the operation. In another example application, the scene is a movie set in which the tracked objects are the bodies of actors for the purpose of replacing them with computer-animated substitutes performing the same motions.

In such applications, the various poses of the tracked objects need to be determined within a typical accuracy of 1:1,000 of the total volume of measurement in each spatial direction, i.e. 1 mm within 1 metre cubed. To date, optical pose tracking systems are considered the most reliable for determining the pose of tracked objects to selected accuracies, and are therefore used in the majority of applications for tracking objects through unstructured scenes. Optical pose tracking systems are commercially available, for example, from Northern Digital Inc. of Waterloo, Ontario, Canada. These systems use two or more optical sensors to optically detect the pose of the tracked objects. Examples of optical systems can be found in U.S. Pat. No. 6,351,661 by Cosman and U.S. Pat. No. 6,351,659 by Vilsmeier, the contents of which are herein incorporated by reference.

Optical pose tracking systems differentiate between tracked and non-tracked objects in the scene by placement of special markers, or "targets", on the objects. A stationary stereoscopic optical sensor, containing two cameras, then repeatedly measures the position and, optionally, the orientation of the individual targets relative to the sensor's own spatial frame of reference, and then reports the measured pose of the targets to a computer for further processing. The computer processor uses the measured pose from the sensor, and prior knowledge of the spatial relationship between the targets and defined points on the objects to which they are attached to calculate the pose of each such object relative to other defined objects or reference frames. However, one disadvantage with current optical tracking systems is that differentiation between the markers and the scene background can be hindered by inadequate illumination of the markers.

In current optical tracking systems, the light energy associated with the targets and sensed by the optical sensors may either be: generated at the target, referred to as active targets; generated near the sensor and reflected by targets coated with a special retro-reflective material, referred to as actively illuminated targets; or an ambient light energy, referred to as fully passive targets. A survey of the types of known optical targets and associated tracking systems appears in the article "An analysis of the properties of targets used in digital close range photogrammetric measurement", T. A. Clarke, SPIE vol. 2350 (1994) p. 251–262, herein incorporated by reference. The article discusses that commercially available pose tracking systems almost universally use either: infra-red LEDs emitters (IREDs) as active targets; or spheres or circles coated with IR reflective 3M™ Scotchlite™ as actively illuminated targets, which are illuminated by infra-red radiation projected from IREDs placed near the sensors. One disadvantage of such systems is that they identify targets by relying upon a strong illumination contrast present between the targets and the background, which is artificially created by the emitted or reflected infra-red radiation. However, the magnitude of the illumination contrast can be affected by a malfunction in the operation of the IREDs and/or obstructions positioned between the optical sensors and the emitted or reflected infra-red radiation.

Alternatively, fully passive systems have a number of inherent advantages over active systems since, by not employing an active infra-red energy source, their optical sensor and target configurations as compared to the active systems have the potential to be simpler, smaller, lighter, less expensive, more reliable, and not dependent upon the projection range of the energy source. Unlike active systems, however, the brightness of targets relative to their surrounding in passive systems cannot be controlled, which can make it difficult to perform the tasks of (1) reliably detecting the presence of targets due only to increased reflection intensity, (2) uniquely labeling each target, and (3) pinpointing each target's pose to a sub-millimeter accuracy over a large measurement volume. Known designs of fully passive systems are such as those described in U.S. Pat. No. 5,792,147, associated UK patent number 2,246,261, and in U.S. Pat. No. 5,603,318, which are herein incorporated by reference. However, these known passive systems have not provided an effective solution to all the performed tasks, and therefore have not been commercially successful.

In particular, U.S. Pat. No. 5,792,147 by Evans at al. describes a passive pointer with a marked predetermined pattern thereon to identify the tip of the pointer in relation to the patient's body, which is then displayed on a monitor with the pre-operative and intra-operative patient images. The border of the pattern in relation to the background is identified using the contrasted edge between the area internal to the target versus the surrounding background area. The predefined patterns are composed of a series of dark-light edges, which are identifiable by an image processing algorithm. Evans et al. describe the use of two high contrast patterns, which are placed in proximity to one another on markers to form the target. The first pattern comprises a complex shape that is not commonly encountered in the selected scene. This recognizable pattern when applied to the marker is used to help uniquely identify and distinguish the target from its surroundings by pattern recognition techniques, on video images supplied by the optical sensors. The second pattern comprises a few straight edges, which are used for incrementally tracking and pinpointing the target's pose.

However, the described patterns and their use in the optical tracking system by Evans et al. have two major limitations. The first limitation is that the image processing operations required to identify the presence of the complex shape, at a wide range of orientations and visible sizes on the video image, are complex and require a substantial amount of CPU overhead. This excessive computation can hinder the application of the targets for real time object tracking.

Further, the target must be held stationery to facilitate the pattern recognition, a situation not always desirable in applications where objects move unpredictably through unstructured scenes. The second limitation is that the method by Evans et al. allows for the incremental tracking of the target's pose, and relies on the target remaining continuously and fully visible while moving a distance of only a few pixels between subsequent measurements. Accordingly, the combination of these limitations results in a termination of pose measurement whenever the target is moved rapidly or when the line of sight between one of the sensor cameras and the target is interrupted. Thereafter, resumption of measurement requires the user to reposition the target in a known location for some period of time to allow the target to be reacquired for subsequent tracking. Other drawbacks of the system by Evans et al. include the need to perform a calibration sequence prior to each measurement session, and a lack of sufficient measurement accuracy for small targets, which require the targets to be relatively large with respect to other objects in the background of the video images supplied by the optical sensors.

Furthermore, in U.S. Pat. No. 5,603,318, Heilbrun at al. disclose a fully passive system in which a complex calibration task is performed prior to each measurement session, similar to Evans et al. Following the calibration task, uniformly colored spherical targets are detected with the aid of background subtraction and edge detection. However, one disadvantage with uniform spherical targets is that they have a widely varying appearance in video images under different lighting conditions, and therefore a static reference background illumination cannot be guaranteed in many operating environments. A further disadvantage is that a sufficient color or intensity contrast may not always be present between each target and its background, e.g. the contour of a white sphere over a white background cannot be distinguished. As a result, the operation of the system by Heilbrun et al. can be inconvenient, unreliable, and inaccurate for target configurations in certain scenes.

It is an object of the present invention to provide an optical pose tracking system and method to obviate or mitigate at least some of the above presented disadvantages.

SUMMARY OF THE INVENTION

The present invention provides real-time computerized measurement of a spatial position and orientation (pose) of specially marked objects moving unpredictably through an unstructured scene. Current optical tracking systems can have difficulties in distinguishing between the markers and the scene background due to inadequate illumination of the markers. Further, the border of the marker in relation to the background is identified using the contrasted edge between the area internal to the marker versus the surrounding background area. However, the marker shapes can have a widely varying appearance in video images under different lighting conditions, and therefore a static reference background illumination cannot be guaranteed in many operating environments. A further disadvantage is that a sufficient color or intensity contrast may not always be present between each target and its background.

Accordingly, the present invention provides a measurement system for tracking a pose of an object displaceable in a coordinate reference frame, such as a three dimensional coordinate system. The system comprises a predefined physical marker adapted for rigidly coupling to the object. The marker can be two or three dimensional in shape. The marker includes a visible target pattern with a series of contrast regions for providing at least two distributed feature points. The contrast regions include an arrangement of alternating dark and bright regions defining an intensity saddle point at their intersection. Each feature point is located at a respective intensity saddle point. The system also has an optical sensor assembly for generating a pair of digital images of the target pattern containing the feature points, wherein the pair of images generated are from dissimilar viewing angles. The system also has an identifier for testing the pixels of the digital images to determine the spatial location in the reference frame for each of the feature points of the target pattern. A marker template including a set of reference characteristics is used to uniquely define a pose relationship between the features points. Further, a processor is used for comparing the determined spatial locations of the feature points to the set of reference characteristics to confirm the recognition of the predefined marker. A method is also described to identify the intensity saddles contained in the digital images. According to the present invention there is provided a measurement system for tracking a pose of a physical marker displaceable in a coordinate reference frame, the system comprising: the physical marker including a visible target pattern with an arrangement of contrast regions for providing at least two distributed feature points; an optical sensor assembly for generating a pair of digital images of the target pattern containing the feature points, the pair of images generated from dissimilar viewing angles; a marker template comprising a unique set of reference characteristics including a relationship between the feature points; and a processor for testing the pixels of the digital images to determine the spatial location in the reference frame for at least two of the feature points of the target pattern, for comparing the determined spatial locations of the feature points to the set of reference characteristics to confirm the recognition of the physical marker, and for calculating the physical marker pose from the spatial location of the feature points.

According to a further aspect of the present invention there is provided a measurement method for tracking a pose of a predefined physical marker displaceable in a coordinate reference frame, the marker including a visible target pattern with a series of contrast regions for providing at least two distributed feature points, the method comprising the steps of: generating a pair of digital images of the target pattern containing the feature points, the pair of images generated from dissimilar viewing angles; testing the pixels of the digital images to determine the spatial location in the reference frame for at least two of the feature points of the target pattern; comparing the determined spatial locations of the feature points to a unique set of reference characteristics for recognising the physical marker in the coordinate frame; and calculating the physical marker pose from the determined spatial locations of the feature points.

BRIEF DESCRIPTION OF THE DRAWINGS

These and other features of the invention will become more apparent from the following description in which reference is made to the appended drawings wherein:

FIG. 6b shows a method for pinpointing projections of the feature points given in FIG. 6a;

DESCRIPTION OF PREFERRED EMBODIMENT

Figure 1:
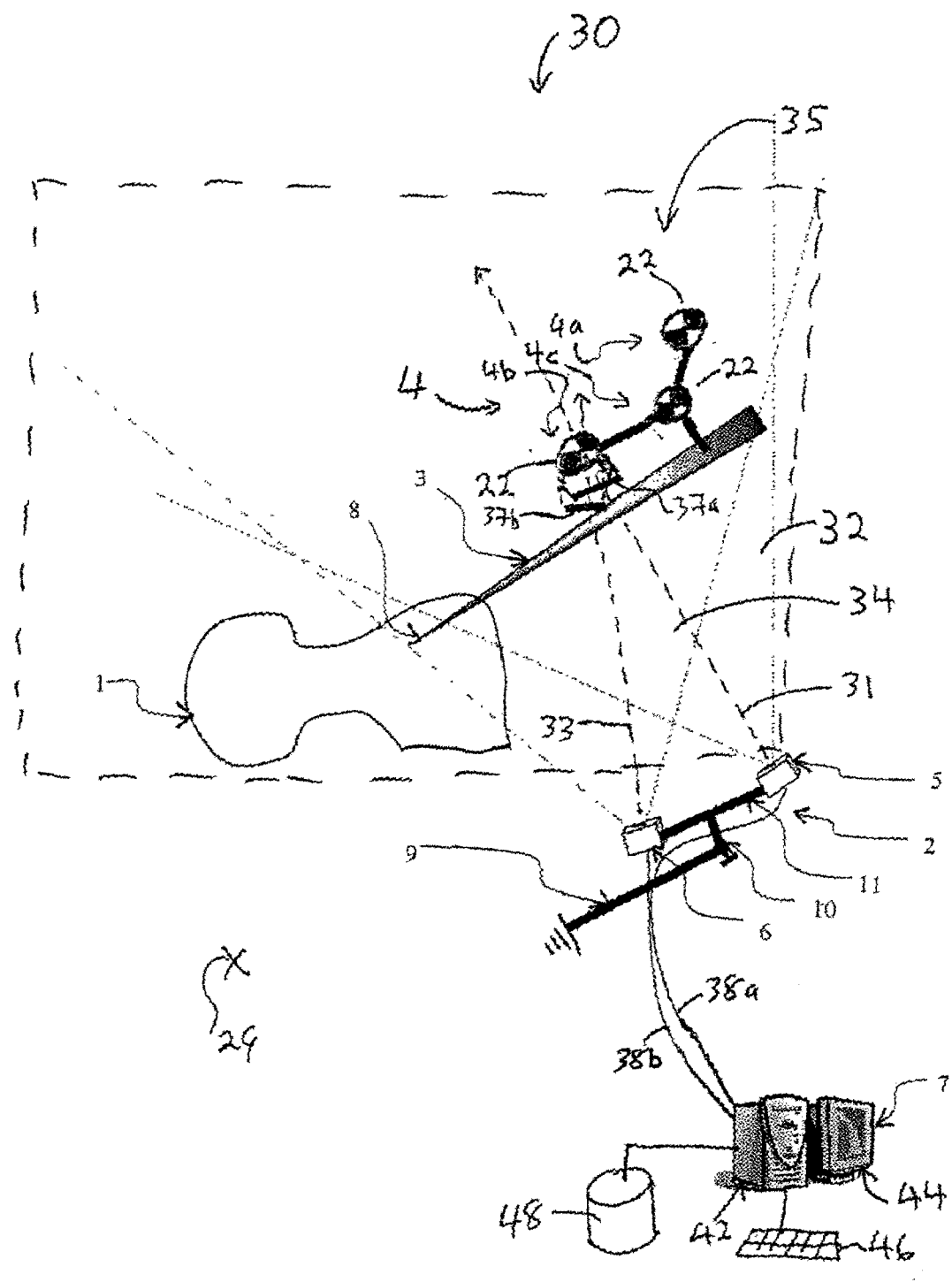
FIG. 1 shows a pose tracking system.

Referring to FIG. 1, a tracking system 30 has an optical sensor assembly 2 used to track the relative position and orientation (pose) of marker 4 attached to an object, such as but not limited to a surgical tool 3 tracked in relation to a portion of a patient's anatomy 1 in a surgical scene 35. The sensor assembly 2 can be a stereo sensor having a first digital video camera sensor 5 with a first field of view 32 and a second digital video camera sensor 6 with a second partially overlapping field of view 34. More than two cameras 5,6 could also be used if desired. Suitable sensors for this purpose are commercially available including, for example, the Mega-D family of stereo digital cameras sold by Videre Design (www.videredesign.com). Such cameras are typically delivered pre-calibrated to allow the association of a pixel position in each of the images with a corresponding linear ray equation in a common sensor 3D space. Otherwise, such calibration may be performed using known methods prior to tracking the pose of marker 4, such as the one described in PCT patent publication WO 01/19273 by Amir et al. It is recognised that such known calibration process include coefficient tables that can be stored in a computer storage medium 48 and made accessible to the position tracking operating software used by a processor 42 of a computer system 7 to determine the relative position of the tool 3 in the coordinate system of the sensor assembly 2.

The position and orientation of the cameras 5, 6 with respect to one another are fixed by rigidly securing the cameras to a support frame 11, so as to provide for the overlapping views 32, 34. The support frame 11 is securely mounted to a fixed support 9, with an adjustable joint 10 to provide adjustment capability to the direction and proximity of the field of views 32, 34 to the surgical arena 35 containing the patient anatomy 1 and the tool 3. The cameras 5,6 have multiple lines of sight vectors 31,33, which are contained within their respective fields of view 32,34. A source of illumination 29 can include ambient light energy (visible light already present at the scene, such as existing room lighting or sunlight), a source of visible or infra-red light radiation advantageously placed near the cameras, or a combination thereof. The targets 4a,b,c can be active targets, actively illuminated targets, or a combination thereof.

A marker 4, composed of a series of flat targets 4a,b,c rigidly positioned with respect to one another, is securely coupled to the tool 3, such that the projection images of marker 4 can be sensed by the cameras 5,6 when positioned in the corresponding fields of view 32, 34. The cameras 5,6 record projections of all items in the scene 35. These image projections are oriented typically perpendicular to the lines of sight 31,33. For example, a projected image 37a,b representing marker 4b would be recorded by the cameras 5 and 6 respectively. A series of image intensity signals 38a,b representing the projected images 37a,b of the targets 4a,b,c are transmitted by the cameras 5,6 to the computer 7, where the signals 38a,b are processed to calculate the three dimensional location of the center of each target 4a,b,c. These signals 38a,b contain image pixel information of the projected images 37a,b for all the objects 3 and markers 4a,b,c present in the scene 35. It is noted that the projected images 37a,b are typically located as formed on a sensor plane (not shown) inside the camera sensors 5,6. Accordingly, the position and orientation of the tip 8 of the tool 3, relative to the pose of the anatomy 1, is determined by the processor 42 of the computer 7 using the known spatial relationship between the targets 4a,b,c and the tip 8, as the tool 3 is moved about the anatomy 1 in the surgical scene 35 during an operation, or about an anatomical model (not shown) for a simulated planning procedure. The position and orientation (pose) information is calculated using the image intensity values of the pixels contained in the signals 38a,b. In this manner, the pose of the specially marked tool 3 is tracked when moving unpredictably through the unstructured scene 35, as further described below. It is recognized a similar marker 4 could be attached to the anatomy 1. It is further recognised that the pose of the anatomy 1 and the tool 3 could also be determined relative to a fixed reference point, such as but not limited to the fixed support 9.

Referring again to FIG. 1, the processor 42 is coupled to a display 44 and to user input devices 46, such as a keyboard, mouse, or other suitable devices. If the display 44 is touch sensitive, then the display 44 itself can be employed as the user input device 46. The computer readable storage medium 48 is coupled to the processor 42 for providing instructions to the processor 42 to perform steps or algorithms related to the determination of the relative spatial position of the tool 3 with respect to the anatomy 1, as well as monitoring the presentation of the anatomy 1 and tool 3 images on the display 44, as further explained below. The computer readable medium 48 can include hardware and/or software such as, by way of example only, magnetic disks, magnetic tape, optically readable medium such as CD ROM's, and semi-conductor memory such as PCMCIA cards. In each case, the medium 48 may take the form of a portable item such as a small disk, floppy diskette, cassette, or it may take the form of a relatively large or immobile item such as hard disk drive, solid state memory card, or RAM provided in the computer 7. It should be noted that the above listed example mediums 48 can be used either alone or in combination to facilitate operation of the tracking system 30.

Figure 2A:
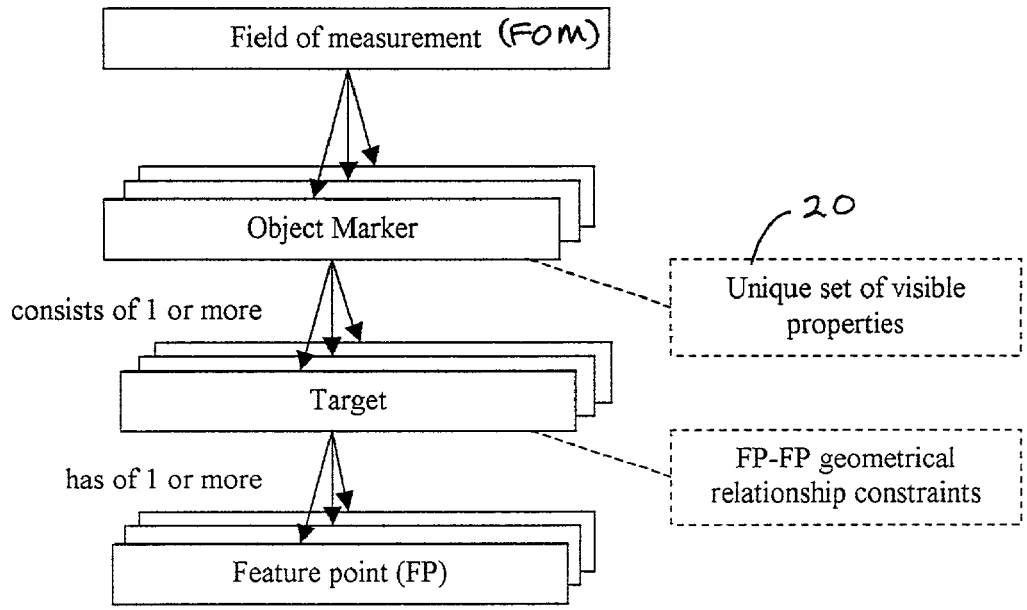
FIG. 2a shows a conceptual model of the key terms used in the description of the system of FIG. 1.

Referring to FIG. 2a, a conceptual model provides example definitions of specific terms used in describing the operation of the tracking system 30. The field of measurement (FOM) is the region of space in which the pose tracking is performed. The FOM extent is defined by the overlap between the fields of view 32, 34 of at least the two video cameras 5, 6 of the sensor assembly 2 (see FIG. 1). Within the FOM, zero or more objects 3 to be tracked are present and may be either stationary or moving. Mechanically attached to each of these objects 3 are one or more object marker 4 with targets 4a, b, c. Each marker 4 in the FOM has its own unique set of visible properties 20 to allow the tracking system 30 to recognize and distinguish between, and correctly label, multiple markers 4 concurrently visible in the FOM. Depending on application-specific design considerations, the geometrical relationship between the pose of the markers 4 and the pose of their attached object 3 may be known to the tracking system 30, or may be known only to the client software application used in the computer 7 deploying the tracking system 30.

Each of the object markers 4 is made up of a set of one or more targets 4a,b,c generically identified by reference numeral 22 (see FIG. 1), each being a visible high-contrast pattern appearing on one or more rigid surfaces of the marker 4. The targets 22 making up the patterned portion of the markers 4 are in a fixed, rigid, geometrical relationship to each other. Each visible target pattern 22 has one or more feature points FP (see FIG. 2b). A feature point FP is an arrangement of light reflectance or emittance properties in the target pattern 22 such that the target 22 will be easy to detect using a pose detection algorithm performed by the computer system 7 under a wide range of marker 4 rotation angles, sizes and lighting conditions. The pose detection algorithm is a computation performed over an image area 24 (see FIG. 6a) of a substantially fixed size (such as, but not limited to, 11×11 pixels) in the image digitized from each camera 5 or 6, which results in a positive or negative determination regarding the likely presence of that feature located in the general vicinity of the middle of the image area 24. When targets optionally contain more than a single FP, the relationship FP—FP between the feature points in each target pattern 22 is defined in order to minimize the occurrence of false target pattern 22 identification, as further explained below.

Figure 2B:
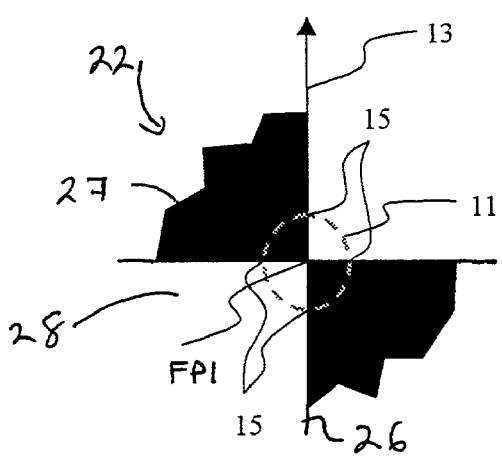
FIG. 2b provides examples of feature point patterns for the system of FIG. 1.

Two preferred embodiments FP1 and FP2 of the feature point FP examples are shown in FIG. 2b, as observed from a direction perpendicular to the flat surface of the marker 4 on which the target pattern 22 is positioned. In both examples, the feature point FP can be defined as an intersection of straight edges 26 formed between alternating dark 27 and bright 28 regions. Such intersections represented by FP1, FP2 do not commonly occur naturally in images and preferably maintain their pattern characteristics of being an intersection FP1, FP2 of straight edges 26 under all viewing angles, magnifications, blurring, and perspective distortion that can be encountered by the camera sensors 5, 6 in viewing the marker 4 in the scene 35. These feature point types FP1, FP2 are also detectable from a wide range of possible appearances in the image using the pose detection algorithm as further explained below. For example, referring to FIG. 2b, stepping along a circle 11 or 18 (such as but not limited to with radius of 3 or 4 pixels) surrounding the feature FP1, FP2 point will yield a fixed number of alternating intensity peaks and valleys (2 each for FP1, 3 each for FP2), and the direction of the intensity gradients (direction of fastest change) at the strongest edges 15 between each such peak and valley pair is substantially tangential to the circle 11, 18. The peaks and valleys of the intensity gradients result from the alternation of dark 27 and light 28 contrast regions located within the circle 11, 18. In addition to the position of the feature points FP in the projected image 37a,b of the target 22, the identification of the FP can further contain an orientation vector 13, which may be defined for example in the case of FP1 to be along the edge 26. This orientation vector 13, when viewed as originating from the FP1 direction, has the dark region 27 on its left and is in the range of 0 to 180 degrees.

It is recognised that the target pattern 22 forms an "intensity saddle" point in its video image which is simpler in peak/valley characteristics than FP2, and, therefore, more likely to appear naturally in image data recorded by the camera sensors 5, 6 and not containing targets 22 (i.e. "imposter" FPs). However, it is considered that FP1 is easier to detect than the more complex pattern of FP2, especially when the projected image 37a,b of the target pattern 22 occupies a relatively small image region of the total background area of the scene 35. Other detection difficulties can include when the target pattern 22 plane is oriented nearly parallel to the line of sight vectors 31,33, or the projected image 37a,b is blurred. Targets 22 may contain more than one type of FP pattern of the sensors 5, 6, as long as the pose detection algorithm is capable of identifying all of those FP types. Preferably, the pose detection algorithm is also capable of differentiating between the FP types, allowing increased flexibility in the design of unique target patterns 22.

The configuration of (i.e., geometrical relationship between) FPs making up a single target 22 is limited by a set of constraints such that there will be only a small likelihood of such FP—FP relationship appearing in each projected image 37a,b where the intended target 22 is not actually present (a false positive identification). In a preferred implementation, at least a subset of those constraints, such as but not limited to alignment or relative orientation, is shared across all targets 22, allowing the presence of any single target 22 to be detected using a generalized target detection algorithm. Other aspects of the configuration of targets 22 may allow variations of one or more parameters, such as but not limited to, relative or absolute distances between FPs, number of FPs, etc. Varying these parameters allows for targets 22 to be differentiated from one another, thereby allowing increased flexibility in designing unique object markers 4.

Figure 3:
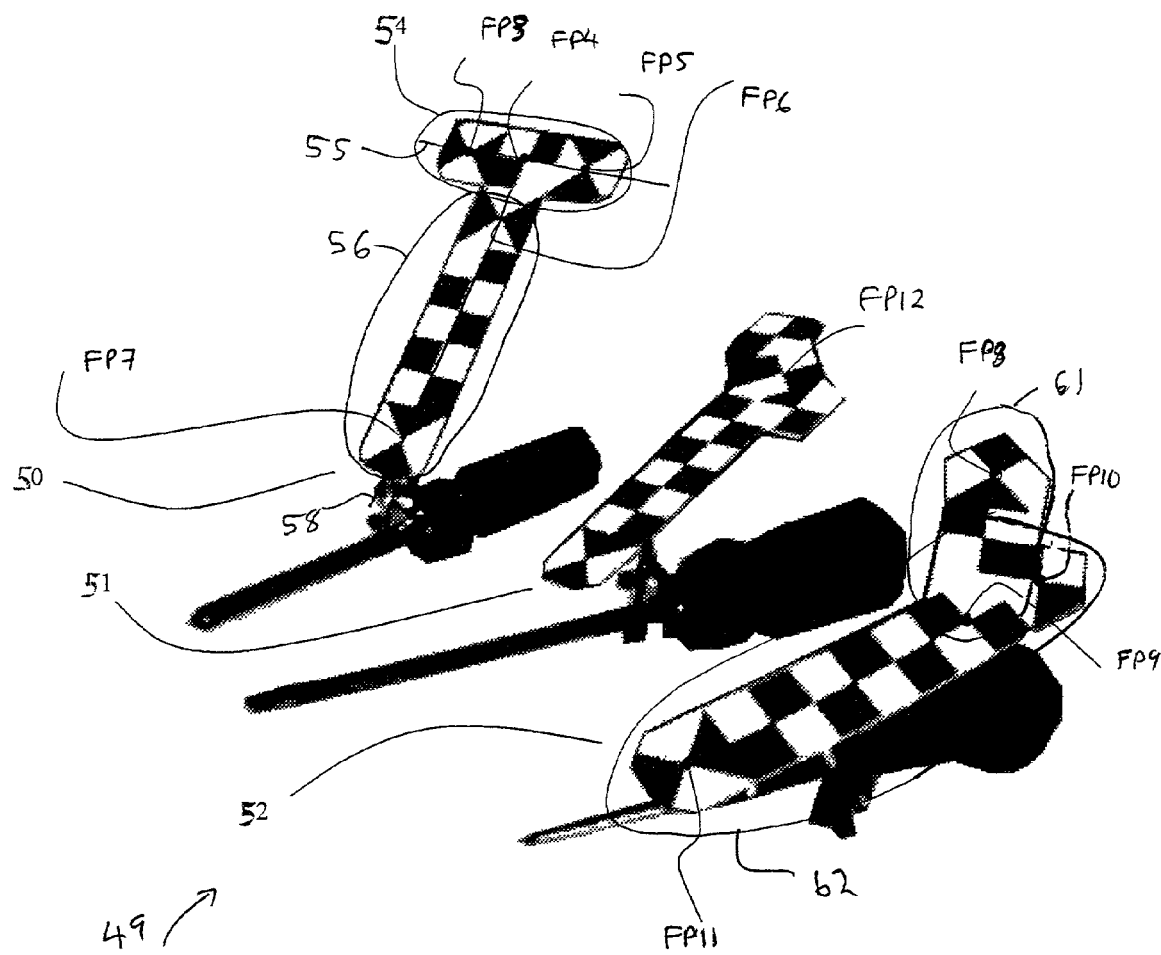
FIG. 3 is an example of a sensor image showing three tools, each with an attached marker, for the system of FIG. 1.

FIG. 3 shows an example of a sensor image 49 obtained from the projected image 37a,b representing the entire scene 35. The image 49 shows three different objects 3 (tools), to which three object markers 50, 51, 52 have been attached. The markers 50, 51, 52 can be made of such as but not limited to a printed plastic or paper sheet with a matte finish, glued to a rigid backing made of hard plastic or metal. All feature points FP, such as FP3, FP4, FP5, FP6, FP7, etc., are of type FP1 in FIG. 2b. A target pattern 54 in this example embodiment is defined as three or more FPs lined up in a straight midline vector 55, where the two outer FPs, FP3 and FP5, are oriented perpendicular to each other, and where all inner FPs, FP4, are oriented diagonally to the outer FPs. The target pattern 54, part of marker 50, is formed by the FPs, FP3, FP4, FP5. This target 54 will be referred to herein as a vector target, since the target 54 defines the straight midline vector 55 which is directed from one end, the base FP (for example, the end FP5 oriented with the bright regions along the midline 55) to the other end, the head FP3. The other FP, FP4, in between those two end points FP3, FP5 referred to as an internal point. For example, target pattern 54 contains the vector 55 with its base at FP5, its head at FP3, and with FP4 as its sole internal point. It is recognized that more than one internal point can be used, if desired, in the vector 55.

A second vector target in the marker 50 is formed by the FPs lying in a straight line 58 starting at FP6 as a base and ending in FP7 as the head, with 4 internal FPs in between. The vector targets 54, 56 may be differentiated by the distance from base to head, the number of internal FPs and the positions of the internal FPs as a fraction of the vector's length (distance from the base FP to the head FP). Accordingly, markers 50, 51, 52 can be differentiated by a combination of the properties of the target vectors 54, 56 they contain and the target vectors' 54, 56 spatial relationship to each other (distances and angles).

Since computing a marker's 50, 51, 52 pose uses the detection and pinpointing of at least 3 points (FPs) in space, the particular markers 50, 51, 52 given in the FIG. 3 provide a degree of redundancy by containing more uniquely identifiable feature points FPs than the 3 minimum points. Therefore, it should be noted that not all FPs that make up the target vector 54, 56 need to be simultaneously observed for it to be identified and measured, and not all the target vectors 54, 56 that make up the marker 50, 51, 52 need to be simultaneously observed to identify and measure the marker's 50, 51, 52 pose as determined by the pose detection algorithm on the computer system 7. This allows for marker 50, 51, 52 detection even when portions of the feature points FP and/or target vectors 54, 56 are partly occluded or when the software fails to correctly identify some of the FPs. When a higher number than 3 FPs in a single marker 50, 51, 52 are observed and pinpointed by the camera sensors 5, 6 in the scene 35, error distribution methods, such as least-mean-square-error (LMSE), can be applied (as discussed later) to help increase the measurement accuracy and to help minimize measurement jitter due to image noise.

To reduce the physical marker 50, 51, 52 size, targets 54, 56 may share FPs, as demonstrated in marker 52, in which FP9 is used both as the base of the target vector 61 whose head is at FP8 and as an internal point of the target vector 62 from base FP9 to head FP11. Similarly, FP12 is shared between the two vectors making up marker 51.

Figure 4A:
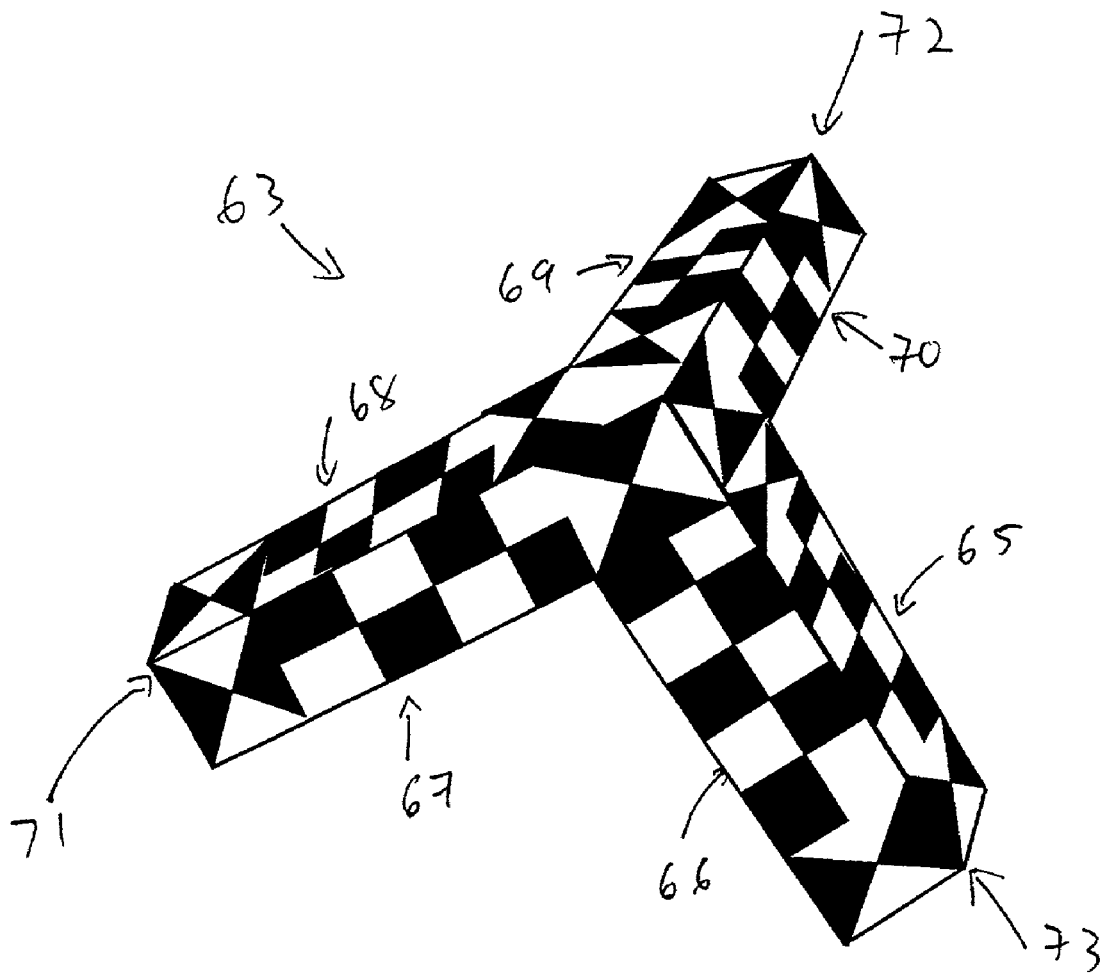
FIGS. 4a, 4b, 4c, 4d provide different marker types than those shown in FIG. 3.

While FIG. 3 shows markers 50, 51,52 with their target patterns 54, 56, 61, 62 lying on a substantially single flat plane, it is sometimes preferable to place the patterns 54, 56, 61, 62 on a three-dimensional surface, for the purpose of increasing the angular range of marker 50,51,52 detection by the camera sensors 5,6. An example of such a marker 63, containing 6 target patterns 65,66,67,68,69, and 70, is shown in FIG. 4a, situated in pairs along the three faces 71,72,73 of the marker 63. The target patterns 65–70 are placed such that each co-oriented pair of target patterns 65–70, 66–67, and 68–69 are facing in a different direction, allowing the sensors 5,6 to identify and pinpoint at least two of the targets 65–70, sufficient for pose tracking, over a wide range of marker 63 orientations.

Figure 4B:
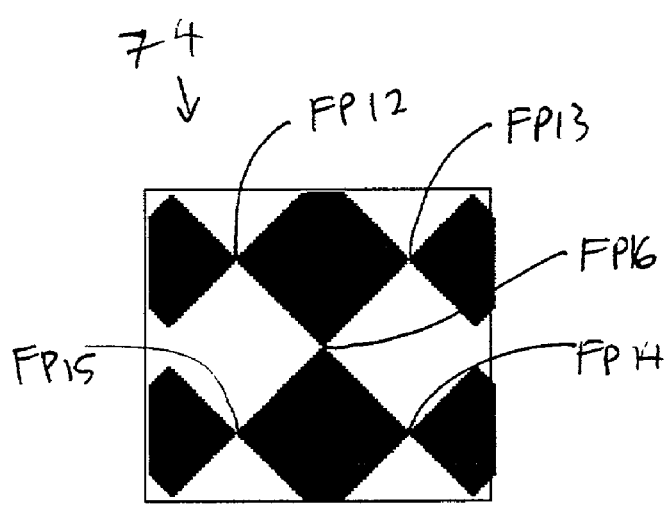

It is recognized that in applications where only a small number of possible objects 3 may appear in the FOM and accuracy is less important, smaller and simpler markers may be used. One such marker 74 is illustrated in FIG. 4b. This marker 74 contains only a single target pattern with five FPs, four of them indicated as FP12, FP13, FP14, FP15 placed at an equal distance from a central FP16. Since the FPs of the marker 74 are not all co-linear, sufficient information is available for computing the marker's 74 pose with some redundancy by the pose algorithm running on the computer 7.

Figure 4C:
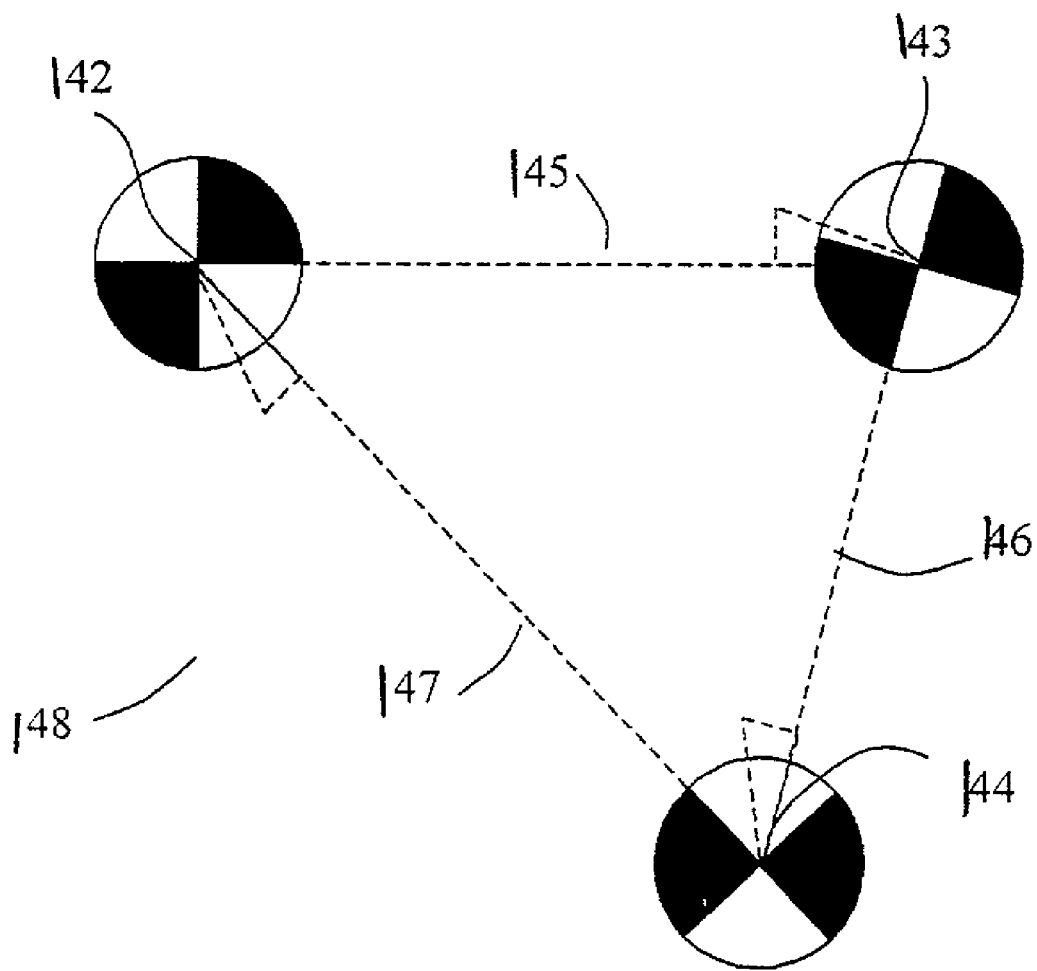

FIG. 4c shows yet another type of marker 148 which can be used in cases where a large marker 148 is needed for increased accuracy, yet the amount of area taken up by the target pattern 22 needs to be minimized so as to reduce the possibility of one marker 148 obscuring other markers 148 from the sensor cameras 5,6. The marker 148 is made up of three FPs: 142, 143 and 144. The FP patterns are oriented to form three imaginary target vectors, 145, 146 and 147, each vector 145,146,147 being defined by two FPs, one of which, at the vector's 145,146,147 base, has one of its two crossing lines accurately aimed at the center of the other FP, at the vector's 145,146,147 head. Each vector pair 145–146, 145–147, 146–147 share an FP 143,142,144 such that the head of one is the base of the other. The imaginary vectors 145,146,147 in FIG. 4c are marked in dotted lines, with a half arrow-head, pointing in the direction of the vector's 145,146,147 head, placed on the darker side of the FP's 142,143,144 crossing line at the vector's 145,146,147 base. If the arrow head is on the right (left) of the vector 145,146,147, the vector 145,146,147 will be termed a "left (right) vector". As with the other types of vectors 145,146, 147 described above, this type of vector 145,146,147 can be identified as such in a projection image 37a,b of the vector 145,146,147, since the property that defines the relationship between the vector's 145,146,147 base and head FPs is maintained in the vector's 145,146,147 projection as well.

Having the freedom to select the direction of the cycle of vectors 145,146,147, clockwise or counter-clockwise, and the side of each vector 145,146,147, left or right, allows for 16 (2 cycle direction×$2^3$ sides) uniquely identifiable markers 148 to be formed using the same three relative FP 142,143, 144 positions. This design can provide economy in manufacturing, since a single rigid marker 148 mold for holding 3 FPs 142,143,144 in their relative spatial positions and orientations can be used, while still allowing for 16 tracked objects 3 to be uniquely identified, The targets containing 142, 143, 144 may be constructed as modular removable plates detachable from a rigid base, allowing them to be factory-sterilized and disposed of following each surgical operation, eliminating the need for sterilizing them subsequent to usage.

Figure 4D:
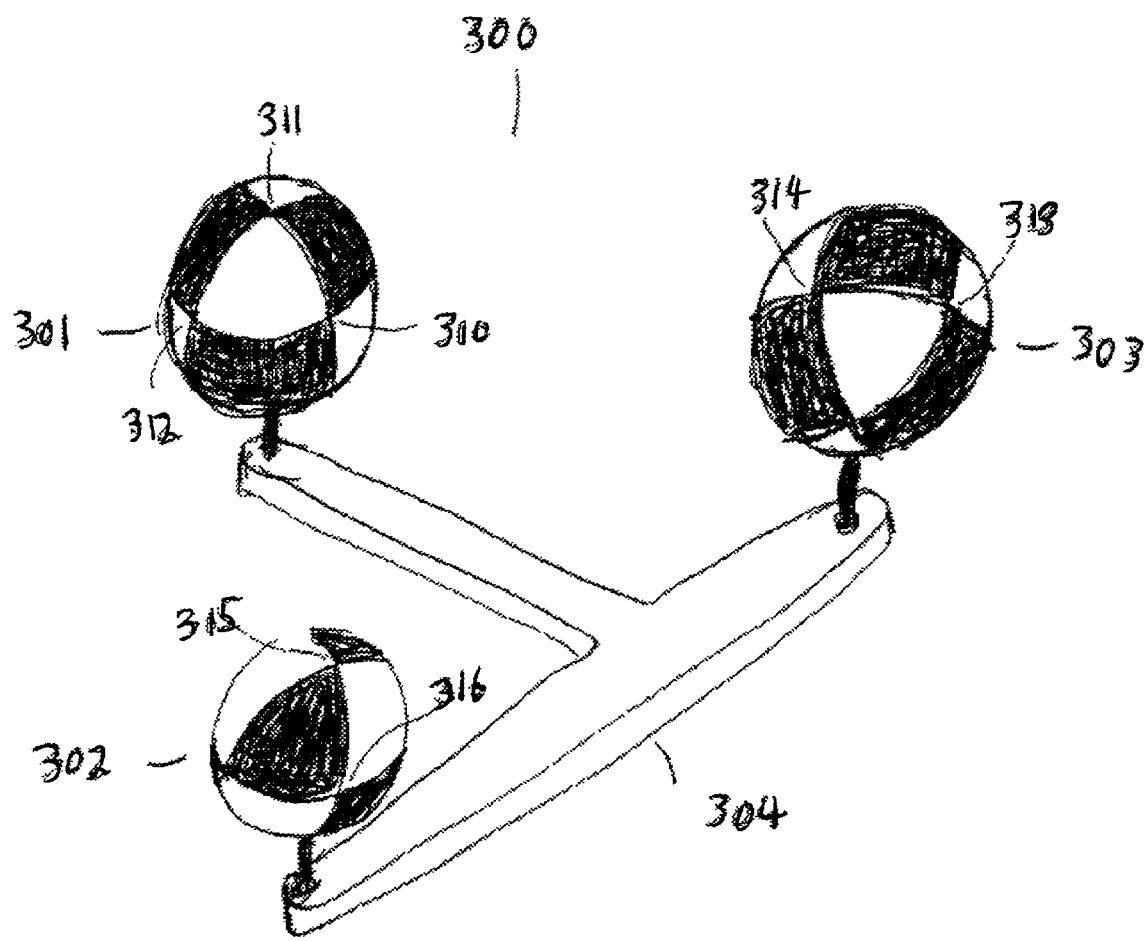

FIG. 4d shows yet another type of marker 300, which, similar to the marker 148 shown in FIG. 4c, minimizes obscuring of other markers, yet allows for a potentially wider angular range of detection by cameras 5,6. The marker 300 consists of spheres 301,302,303 secured in fixed relative poses to a base 304. FPs 310–316 have been formed on the surface of each sphere 301,302,303 at the intersections of circular target patterns drawn on the sphere's 301,302,303 surface, by alternating dark and bright regions between those circles as shown. Some of such FPs 310–316 are shown. The placement of FPs 310–316 on each circular pattern is chosen to ensure that at least a single FP 310–316 on each sphere 310,32,303 will be simultaneously visible by both cameras 5,6 at the desired range of marker 300 orientation with the FOM.

Figure 2B:
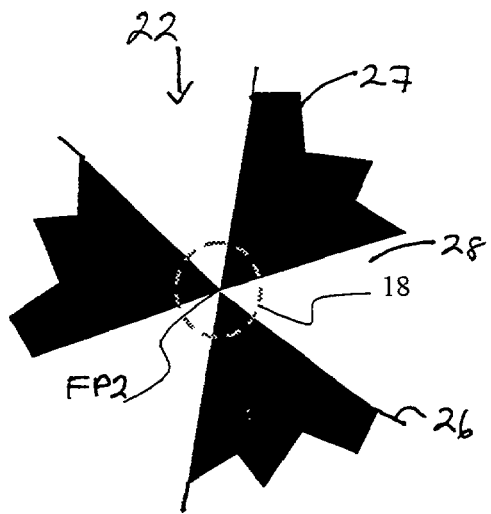
Figure 5:
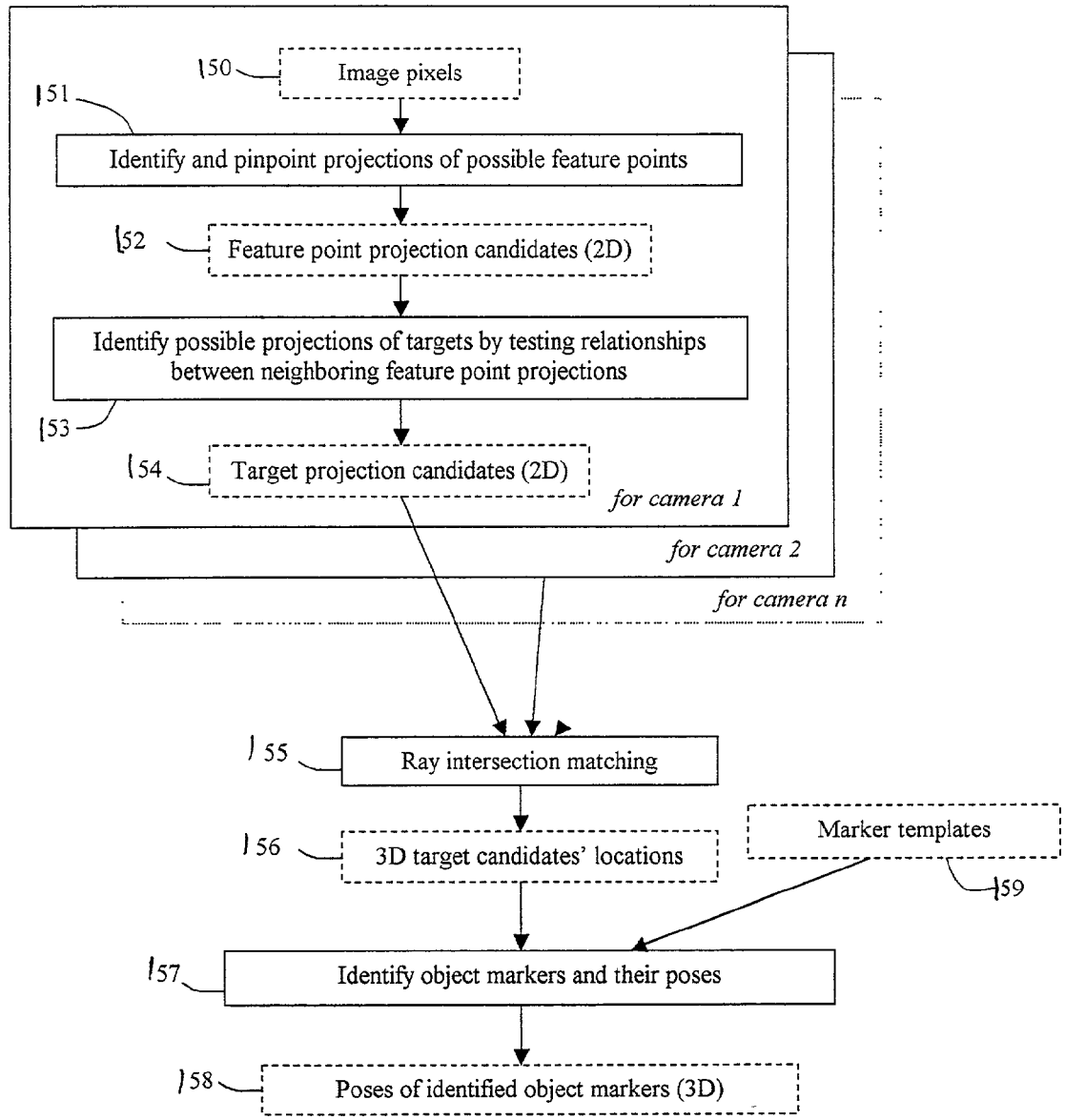
FIG. 5 is a flow chart of the method for identifying poses of the markers used in the system of FIG. 1.

The method by which the presence and poses of object markers 4, 50,51,52, 63, 74 and 148 in the FOM are computed from the sensor images is outlined in FIG. 5. Data elements are represented by dashed boxes, while method steps consisting mainly of active computation using the respective data as input, or generating the respective data as output, are placed in solid boxes. Buffers of image pixels 150 are obtained by the computer 7 from the sensor assembly 2, one per camera 5,6. In step 151, an operation is performed on a small environment around some or all of the image pixels to detect the likely presence of the FPs at, or near, the examined pixels. In the preferred embodiment, the projection of the FP forms an intensity saddle 173 (see FIG. 6a) in the image area 24. While the orientation and width of the alternating dark 27 and bright 28 regions around the saddle point 173 are unknown, a point test can first be performed to reject approximately 99% of the pixels in typical projected images, allowing secondary or additional, more discriminating, tests to be performed only on the small minority of pixels that passed the point test, as further explained below. An example of such a point test examines the image values of pixels lying on the circle 11,18 (see FIG. 2) of some small radius (such as 3 or 4 pixels) around the candidate FP pixel potentially located at the saddle point 173 (see FIG. 6a), iteratively comparing the values of two pixel pairs located at the ends of perpendicular diameters of the circular region 11,18. If no two such pixel pairs exist where the maximum pixel value in one pair is lower than the minimum pixel value in the other by a predetermined threshold value, that pixel is rejected. Since the diameter of the circle 11,18 is relatively small and the tested pixel positions relative to the central pixel, representing the candidate FP, are identical for all pixel locations, this test can be efficiently coded.

Further optimization techniques in step 151 allow FP detection to achieve real-time rates (30 Hz) using economically available computation power (such as in a desktop PC) of the computer system 7 when the sensors 5,6 provide two VGA (640×480) resolution images represented in the data signals 38a,b. It is recognized that more than two sensors 5,6 and corresponding signals 38a,b can be used, if desired. These optimization techniques include:

Multi-resolution processing: Using a decimated (sub-sampled or averaged-down) images of the scene 35 to reject regions that do not contain FPs. Decimated locations may be rejected when their surrounding region does not contain a sufficient number of edge pixels or sufficient intensity variation represented by the dark 27 and bright 28 regions.

Change detection: Dividing the image of the scene 35 (full resolution or decimated) into regions, possibly overlapping, and comparing the pixel values of each region with the values of that region in a previously captured image to detect a change larger than video noise. If no such change is detected, the previous presence of FPs in that region is assumed for the current measurement cycle as well.

Edge orientation template: Dividing the image of the scene 35 (full resolution or decimated) into overlapping regions, and rejecting regions where an insufficient number of edge locations (where a gradient strength between the dark 27 and bright 28 regions exceeds a threshold) demonstrate a local edge orientation that is substantially radial to the region's center. A fast implementation of such comparison uses a radial (or, equivalently, tangential) orientations template and a comparison look-up table.

Edge orientation histogram: Dividing the image of the scene 35 (full resolution or decimated) into overlapping regions, and rejecting regions where a smoothed histogram of edge orientations does not show at least the required minimum number of peaks (eg, 4 contrast peaks for the FP1 pattern, 6 contrast peaks for FP2 pattern in FIG. 2b).

Fast tracking slow detection: Examining all locations in the vicinity of FP locations predicted by extrapolation from earlier measurements (to maintain tracking of known markers 4), but only a portion of the pixels in other areas (to detect new markers 4 that entered the FOM). This technique allows fast tracking of markers 4 already detected, but will exhibit some delay in locating new markers 4.

The selection of optimization techniques used by the tracking system 30 depends on the specific application and capabilities of the computing hardware of the computer system 7. For example, in applications where the sensors 5,6 are static in relationship to the scene 35 and only a small portion of the image representing the scene 35 is expected to show motion, change detection can be effective. In applications where some delay in detecting the presence of new markers 4 is acceptable and the hardware of the computer system 7 is not fast enough to achieve the required pose-tracking rate, the fast tracking/slow detection optimization can be useful.

Using a combination of optimization techniques and the initial point test, only a small fraction of the image locations contained in the scene 35 (typically 1% or less) need to be further assessed to confirm or reject the presence of the FPs in the projected image 150. Often, a number of nearby pixels around each FP projection will all pass the initial point test.

Since FP projection locations are separated by some minimum distance (eg, 10 pixels) from each other, the number of candidate FP pixels can be further decimated by replacing clusters of neighboring FP candidates with a single FP candidate at the center of the cluster. Finally, a number of more discriminating secondary tests are applied to the remaining candidates, to help eliminate false identifications, usually resulting from narrow low/high intensity strips or measurement noise. Such secondary tests may include, for example, detecting edges within the small circular environment 11,18 around the candidate FP pixel, and then evaluating the degree to which the edge locations and their orientation fit the FP pattern of two crossing lines 15 (see FIG. 2b) which reverse the edge direction when passing through the center of the circular region 11,18. Performed on a relatively small environment (eg, 11×11 pixels), such tests can yield the desired results regardless of the rotation and view angle (within ±60 degrees of the perpendicular) of the projected image 37a,b to the line of sight vectors 31,33 (see FIG. 1) or the degree in which the FP is in focus (since an out-of-focus intensity saddle point 173 remains a saddle point 173). It is recognized that shaped regions other than circular 11,18 could also be used in the tracking system 30, if desired.

Preferably at the completion of the more rigorous secondary tests, the locations of successful FP candidates are pinpointed to sub-pixel accuracy. A number of sub-pixel target pinpointing methods are known in the art. See, for example, "A comparison of some techniques for the sub-pixel location of discrete target images", Shortis et al., SPIE vol. 2350 (1994) p. 239–251. Known methods, however, were developed for a bright round target on a dark background (or vice versa) and are thus unsuitable for the purpose of pinpointing the intensity saddle point 173. An example method for identifying a grouping of intensity points 174 to pinpoint the pose of the candidate FP located at the saddle point 173 is described next, in reference to FIGS. 6a and 6b.

Figure 6A:
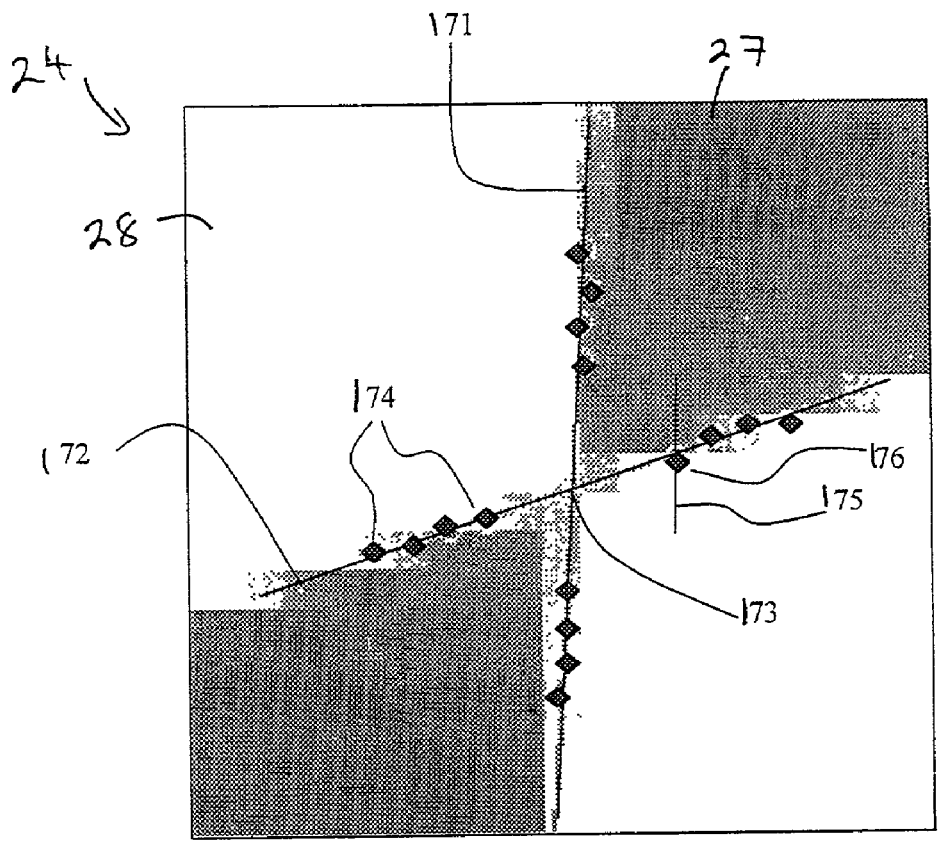
FIG. 6a shows example feature point determination for the markers used in the system of FIG. 1
Figure 6B:
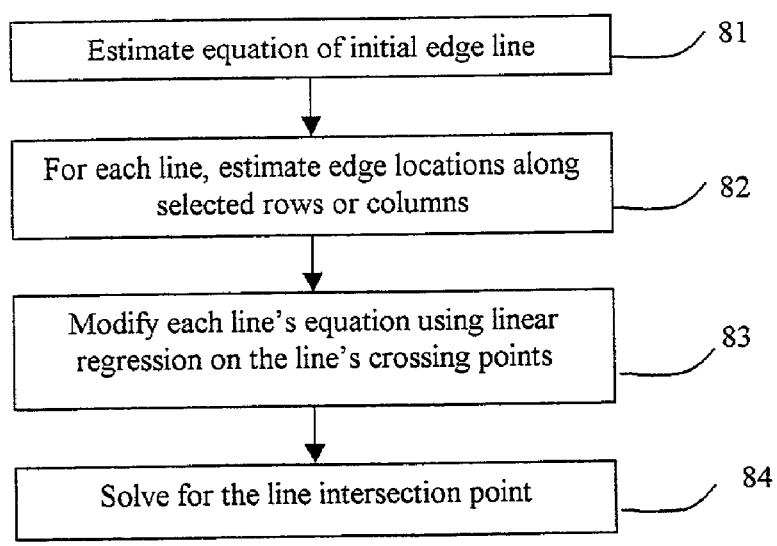

FIG. 6a shows an enlarged image region 24 surrounding a candidate FP location 173 approximately at its center. The pinpointing method itself is described in FIG. 6b with reference to FIG. 6a. This pinpointing is performed in the step 151 of testing the validity of FP candidates to result in the identification of the intensity saddle points 173. In step 81, the location of two crossing edge lines 171 and 172 is coarsely estimated. In step 82, for each of the two edge lines 171,172, a range of rows or columns is selected by the processor 42 of the computer 7 in the pixel image region 24, and the exact edge location along each row or column is estimated. If the line 171, 172 is substantially horizontal, columns 175 are selected, and vice versa. In selecting the rows or columns, a minimum distance of 2 or 3 pixel units away from the estimated feature point location is used to help avoid the central area where pixel intensities are simultaneously affected by both edges. In the example shown in FIG. 6a, eight columns 175 have been selected for line 172, four consecutive columns on each side of the region's center 173, starting in the third column away from the estimated center 173. At each column 175 a search for the exact edge location 176 at a sub-pixel resolution is performed using one of a number of known edge detection methods. For example, a high order curve may be fitted to the pixel intensity values 174 on the lines 171,172 along each column 175, and the edge location is estimated to be where the curve obtains the middle value between the dark and bright plateaus of the curve. In step 83, a linear regression is performed on the set of edge locations estimated for each line, and each line equation is replaced by the results of the regression. Finally, in step 84, the exact location of the feature point FP located at the intensity saddle point 173 is calculated by solving for the intersection of the two lines 171,172. In cases where FP may be formed on surfaces which are not flat, for example in the case of marker 300 shown in FIG. 4d, higher-order curves are fitted to the estimated edge locations, and the linear regression is replaced with another known higher-order curve-fitting algorithm that helps to minimize the effect of small point displacement errors, for example by a bezier curve interpolator.

Returning now to FIG. 5, a set 152 of candidate image locations is generated from the results of step 151, where a projections of the FPs is likely to be found. This set typically contains all of the real target FP projections in the FOM, but, in addition, a number of additional points that have similar local intensity characteristics but are formed by light reflecting from other objects in the scene 35.

In step 153 a search is conducted to detect sets of FP projection locations that comply with the restrictions placed on FPs participating in the same target pattern 54,56,61,62 (see FIG. 3). In one embodiment with reference to FIG. 3, target patterns 54,56,61,62 are defined as planar vector patterns complying with the abovementioned restrictions of having a base FP, a head FP and one or more internal FPs between them, all co-linear. These restrictions can be tested in a 2D projection of the vector 55,58, since a linear projection of the target patterns 54,56,61,62 exhibits the same restrictions. To improve the efficiency of the search, it is done hierarchically. First, each candidate FP is evaluated with respect to a small number of its closest neighbors, to discover, based on the orientation of their edge lines, whether they form an FP pair that may belong in the vector 55,58. Such possible FP pairs include base-internal (base link), head-internal (head link) and internal-internal (internal link). Next, each combination of base link and head link is tested to see if all related FPs are positioned in a co-linear orientation with respect to one another as a group, and, when they are, whether a sequence of internal links sharing a common FP can be formed to define the vector 55,58 there-between.

The result of step 153 is a list of target projection candidates 154 for each of the sensor cameras 5,6. All FP candidates that do not belong to any target candidate as identified in step 154 can be ignored in subsequent processing steps. These projection candidates 154 most likely contain projections of all the true target vectors 55,58, but will often contain some additional vectors, falsely identified due to the tolerances allowed when testing for compliance with target configuration restrictions (such as co-linearity).

In step 155, the lists of identified target pattern projections 154 for the different sensor cameras 5,6 are combined to establish the 3D positions of candidate target patterns 54,56, 61,62. Using calibration data stored in the computer storage 48, rays corresponding to base and head FP projections are calculated per camera 5,6. For each possible combination of target projections identified by different cameras 5,6, the shortest distance between the camera-specific rays corresponding to the base and the head of the vector 55,58 is calculated. Only target projection combinations where the closest ray distance at both ends falls below some tolerance (eg, 1 mm) are considered projections of the same candidate target pattern 54,56,61,62. For these candidates, the 3D estimated locations of all the matched FPs (base, head and internal) are calculated using ray intersection estimation methods as is known in the art, and the target candidate is added to the list of identified 3D target candidates 156. Target candidates list 156 now contains a list of all target vectors 54,55,61,62 identified in the FOM, each with its FP 3D positions. It is possible that there are multiple possible solutions to the matching of projections of target patterns 54,56,61,62. In such cases, list 156 will contain targets representing multiple mutually exclusive vector target projection matching possibilities.

In final step 157, the list of target candidates 156 is evaluated against a database stored in the computer storage 48 of known marker templates 159, each containing the true geometrical characteristics of the identified markers 50,51, 52. To allow each marker's 50,51,52 pose to be fully specified, the marker 50,51,52 contains at least two vectors 55,58. It may, however, contain more than two vectors, for example to allow a wider detection angle between the markers 50,51,52 surface plane and the line of sight vectors 31,33 (as demonstrated in FIG. 4a) or to increase immunity against partial occlusion of the marker from one of cameras 5,6. The tracking system 30 therefore identifies and reports on the pose of each marker 50,51,52 even if only a portion of its vectors 55,58 are detected, as long as this portion contains at least two vectors 55,58.

Each marker template 159 data contains sufficient information to uniquely identify each possible pair of vectors 55,58 that can be simultaneously observed, which uniquely identify the target patterns 54,56,61,62 making up each of the markers 50,51,52. For example, in FIG. 3, vectors 55, 58 represent target patterns 54,56 respectively which then make up marker 50. The template data can contain the distances between the one vectors' end FPs (base and head) and the other's end FPs. The markers 50,51,52 are constructed such that in the set of distances between FPs in every two vectors 55,58 it contains there is at least one distance that is sufficiently different from any other such set of distances in the same or other templates, so as to prevent misidentification in step 157 between the target patterns 54,56,61,62 present on the various markers 50,51,52. Given the wide flexibility in choosing sizes, angles and relative placement of vectors 55,58, this restriction can allow for a great many different templates to be designed. The templates stored on the storage 48 also describe the distances between each vector's 55,58 base FP and its internal FPs. If necessary, it is possible to further increase the number of possible marker 50,51,52 variations by including the positions of internal FPs in the matching criteria applied in step 157.

In performing step 157, the distances between the end FPs of each possible pairs of candidate vectors 55,58 are exhaustively compared against the corresponding sets of distances in the marker 50,51,52 templates. A match is declared when none of the distance comparisons discovers a discrepancy higher than some specified tolerance (eg, 2 mm). The pose of the identified marker 50,51,52 within the sensor 5,6 fields of view 32,34 is then computed at step 158 using one of several known algorithms for paired-points registration, such as but not limited to an iterative search for the linear 3D transform that minimizes RMS position error. All matched FPs contribute to the registration, including the internal ones. It should be noted that the larger the number of FPs matched, the less the pose measurement is sensitive to image noise and local calibration errors.

Figure 7:
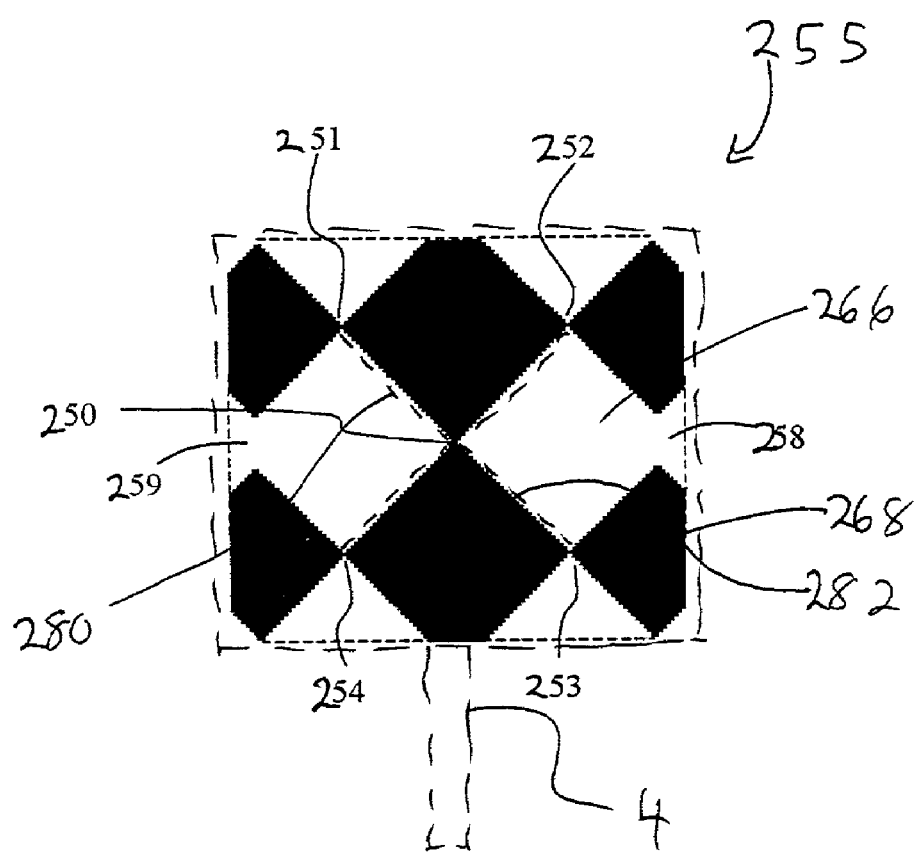
FIG. 7 is an alternative method of use for the pattern shown in FIG. 4b.

Referring to FIG. 7, a further embodiment of a target pattern 255 has five intersection points 250, 251, 252, 253, 254, where corners of two relatively light 266 (or white) and two relatively dark 268 (or black) regions meet. The regions 266, 268 are of uniform shade, and preferably made of a non-reflective material, with their edges straight, meeting at right angles at each intersection point 251, 252, 253, 254. The pattern 255 is positioned on the flat surface of a marker. It should be noted that the gaps 258 and 259 help to inhibit their identification of their locations as intersection points.

Figure 8:
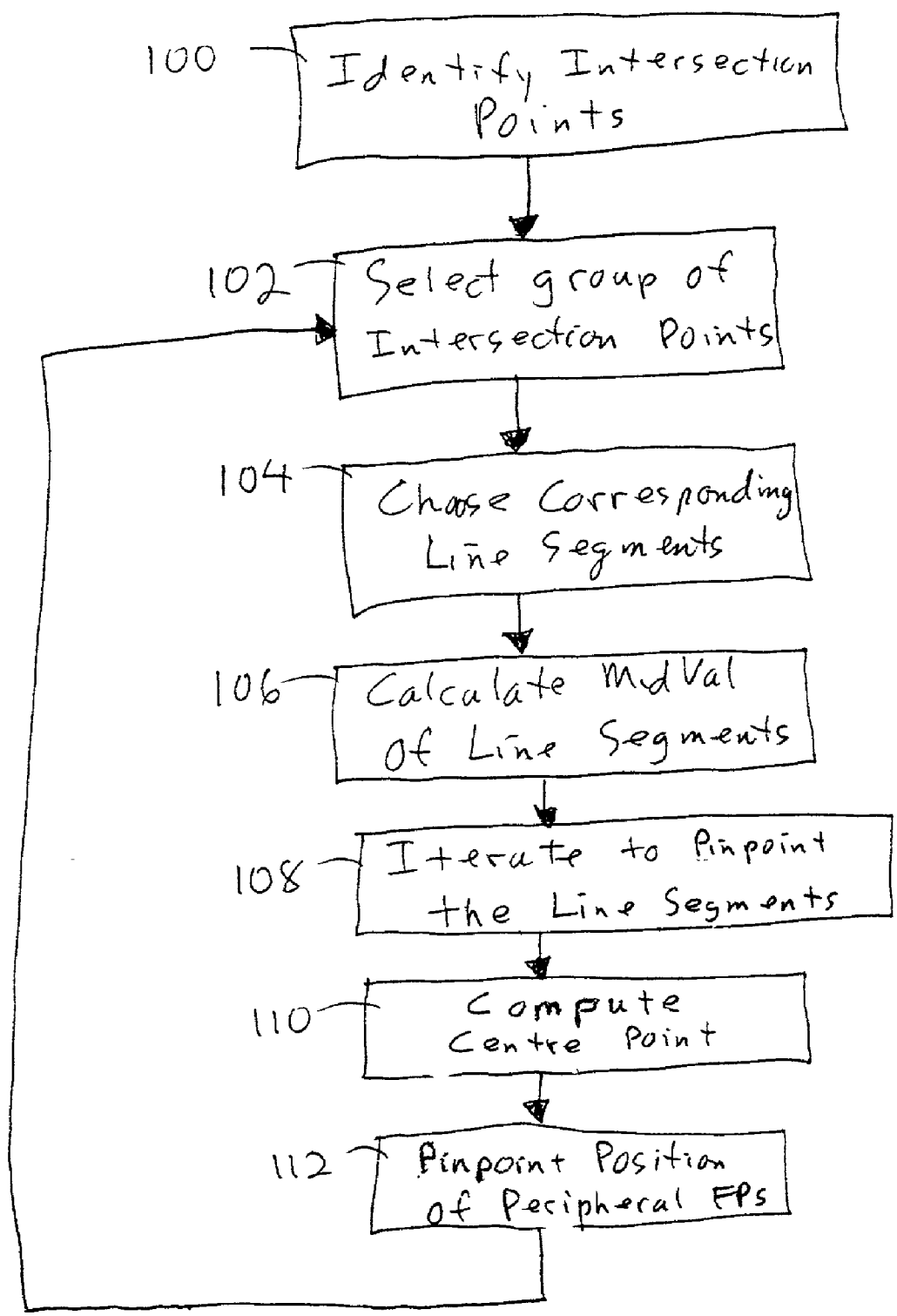
FIG. 8 is an alternative method of detection of feature points shown in FIG. 7.

Referring to FIG. 8, a further embodiment target detection localization algorithm is as follows for identification of the target pattern 255, by the processor 42, from the digital images 49 supplied by the cameras 5,6 of the sensor assembly 2. This algorithm combines steps 151 and 153 (FIG. 5). For each camera 5,6, the processor identifies in step 100 all the intersection points 250, 251, 252, 253, 254. The processor 42 then identifies the individual target patterns 255 by selecting, in step 102, groups of 5 FPs that match a predefined target pattern 255 criteria of having 4 peripheral FPs 251, 252, 253, 254, at substantially the same distance from the fifth center FP 250, and of the arrangement of the FPs along two intersecting lines 280, 282 in an X-like formation. Accordingly, for each individual target pattern 255 selected, each of the line segments 280, 282 is chosen 104 that connect opposing pairs of intersection points 251,253 and 252, 254 respectively. Then, a MidVal is calculated 106 by averaging the pixel intensity values of the light regions 266 on one side and the dark regions 268 on the other side of each line segments 280, 282. The processor 42 then iteratively adjusts 108 the position and orientation of the chosen line segments 280, 282 to minimize the root mean square error (RMS) between bi-linearly or bi-cubically interpolated pixel intensity values sampled along the selected lines 280, 282 and the MidVal. The exact sub-pixel position of the pattern's 255 center FP 250 is then computed in step 110 as the intersection of the two line segments 280, 282. In step 112, the sub-pixel positions of peripheral FPs 251, 252, 253, 254 are computed by evaluating the intensity difference in a direction perpendicular to lines 280, 282 in the vicinity of each estimated FP position, and computing the zero crossing location of that difference (i.e. the interpolated location where it changes sign).

Figure 9:
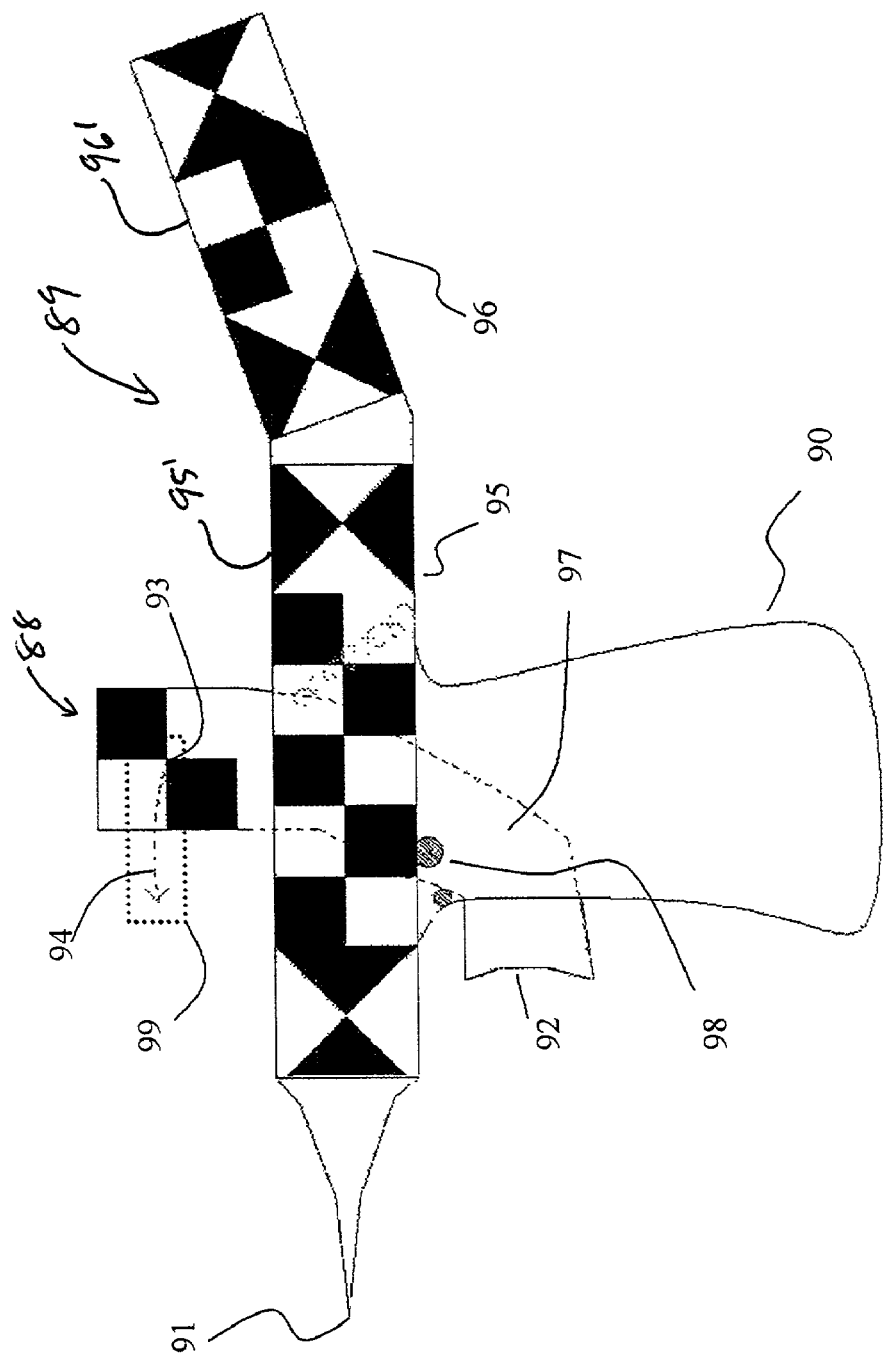
FIG. 9 is a further embodiment of a tool with a marker and an additional movable feature point used to obtain additional user input.

A further embodiment of the tracking system 30 is given in FIG. 9, which allows people holding tracked objects 3 to indicate one or more input values to the tracker's software (operating on the computer system 7) client application while helping to minimise the use of additional electronics. In the example, a pointer 90 is used, with the aid of the current invention, to input specific locations, such as observed anatomical features of a patient 1 undergoing surgery, to a software program, such as a surgical image guidance application operating on the computer system 7. An additional on/off input value may be used to inform the application that the pointer 90 is at a specific anatomical feature 1 of importance, or a smoothly varying value may be used to control one of the display parameters of the anatomy 1 on the display, such as the relative depth of an image cut plane showing the anatomy 1 below the pointer's tip 91.

Target patterns 95 and 96 form a marker 89, which is positioned on the body of the pointer 90. The target patterns 95,96 allow the pose of the pointer 90 to be sensed and reported by the tracking system (see FIG. 1) as described above. Two additional target patterns 95',96' are marked on the right (hidden) side of the pointer 90 on hidden side of the target patterns 95,96, to allow the sensors 5,6 of the sensor assembly 2 to be positioned to either side of the pointer 90. Pressing a trigger 92 of the pointer 90 causes a plate 97 holding the target pattern 88 to rotate around an axis 98, moving a feature point 93 of the target pattern 88 forward as indicated by dashed arrow 94. A pointer template, stored in marker templates database 159 (FIG. 4), contains data regarding the position and orientation of the pointer tip 91 relative to vectors contained by the target patterns 95 and 96. It further contains information regarding the boundary of a region 99 in which input-value FP 93 may be found over its full range of motion, and the two extreme positions of FP 93 within that region (idle and fully triggered). Once the software of the tracking system 30 has identified pointer 90 in the FOM, it takes notice of the additional information stored in its marker template. The tracking algorithm then searches for FP 93 within the projections of region 99 in all sensor images, calculates the relative travel fraction of FP 93 between its two extreme positions through tracking the pose of the target pattern 88, and reports that fraction to the application, together with the pose of tip 91, as inferred from the pose of the marker 89 containing the target patterns 95,96,95',96'. Accordingly, the application may use that fraction to determine whether the user indicates one of two binary input values (on/off), or some intermediate value, as appropriate for the intended use.

It is noted that a minimum of two FPS can be located on the target patterns for tracking the pose of the associated markers, such as but not limited to in the measurement of 5 degrees of freedom such as discarding rotation about an axis of the coordinate frame. Further, tracking motion in a plane could also be done with an appropriate number of FPs present to determine the pose of the tracked marker in the plane. The overall target pattern on the marker can include an arrangement of individual target patterns with at least one feature point FP on each individual target pattern.

Although the invention has been described with reference to certain specific embodiments, various modifications thereof will be apparent to those skilled in the art without departing from the spirit and scope of the invention as outlined in the claims appended hereto.

What is claimed is:

1. A measurement system for tracking a pose of an object displaceable in a coordinate reference frame, the system comprising:
   a) an optically visible target pattern secured to the object, the target pattern containing an arrangement of contrast regions for defining at least two feature points, each feature point being located at a juncture of an optically detectable plurality of edges, wherein each edge in the optically detectable plurality of edges separates different contrast regions;
   b) an optical sensor assembly for generating a pair of digital images of the target pattern containing the feature points, the pair of images being generated from dissimilar viewing angles;
   c) a marker template comprising a unique set of reference characteristics including a relationship between the feature points; and,
   d) a processor for testing the pixels of the digital images to determine the spatial location in the reference frame for each of the feature points of the target pattern, for comparing the determined spatial locations of the feature points to the set of reference characteristics to confirm the recognition of the target pattern, and for calculating the object pose from the spatial location of the feature points.

2. The system of claim 1 further comprising at least three feature points to define a pair of non-collinear target vectors.

3. The system of claim 2, wherein at least four feature points define the pair of non-collinear target vectors.

4. The system of claim 2, wherein a plurality of the feature points defines at least three non-collinear target vectors.

5. The system of claim 2 further comprising a plurality of target patterns with at least one of the feature points present on each one of the plurality of target patterns.

6. The system of claim 2, wherein the reference characteristics are selected from the group comprising a distance between the adjacent feature points, the number of feature points, a distance between adjacent target vectors, and an angle between adjacent target vectors.

7. The system of claim 1 wherein the contrast regions include a plurality of alternating dark and bright regions.

8. The system of claim 7 further comprising an intensity gradient between adjacent pixels in the digital images, one of the adjacent pixels being in one of the dark regions and the other of the adjacent pixels being in one of the bright regions.

9. The system of claim 8, wherein a distribution of intensity gradients corresponding to the alternating dark and bright regions defines an arrangement of alternating intensity peaks and valleys.

10. The system of claim 9, wherein each of the feature points is an intensity saddle located in the center of the arrangement of alternating peaks and valleys.

11. The system of claim 10, wherein the type of the feature points is determined by the number of peaks and valleys associated with each of the feature points.

12. The system of claim 11, wherein the feature point type is included in the reference characteristics.

13. The system of claim 1 further comprising a plurality of target patterns, each of the target patterns having at least one feature point.

14. The system of claim 13, wherein each of the target patterns contain a respective set of at least two of the feature points.

15. The system of claim 14, wherein the respective set of feature points defines a corresponding target vector.

16. The system of claim 15, wherein each of the target vectors is oriented in a unique direction.

17. The system of claim 16, wherein the plurality of target patterns are located on a planar surface.

18. The system of claim 16, wherein at least one of the target patterns is located on a three dimensional surface.

19. The system of claim 16, wherein at least one of the target patterns is positioned on a corresponding one of a plurality of planes, and each of the planes is oriented in a different direction.

20. A measurement method for tracking a pose of an object displaceable in a coordinate reference frame, the method comprising the steps of:
   a) providing a visible target pattern on the object, the visible target pattern having an arrangement of contrast regions for defining at least two feature points, each feature point being located at a juncture of an optically detectable plurality of edges, wherein each edge in the optically detectable plurality of edges separates different contrast regions;
   b) generating a pair of digital images of the target pattern containing the feature points, the pair of images being generated from dissimilar viewing angles;
   c) testing the pixels of the digital images to determine the spatial location in the reference frame for at least two of the feature points of the target pattern by determining the juncture of the optically detectable plurality of edges for each feature point;
   d) comparing the determined spatial locations of the feature points to a unique set of reference characteristics for recognizing the target pattern in the coordinate frame; and
   e) calculating the object pose from the determined spatial locations of the feature points.

21. The method of claim 20, wherein the step of testing the pixels includes a first point test for rejecting a majority of the pixels not containing candidate feature points.

22. The method of claim 21 further comprising the step of applying a second test for identifying the feature points from the remaining pixels containing the candidate feature points.

23. The method of claim 21, wherein the first test for the image pixels is selected from the group comprising multi-resolution processing, change detection, edge orientation template, edge orientation histogram, and fast tracking slow detection.

24. The method of claim 22, wherein the second test for the image pixels is selected from the group comprising multi-resolution processing, change detection, edge orientation template, edge orientation histogram, and fast tracking slow detection.

25. The method of claim 20, wherein step c) comprises locating a pair of edge lines in the plurality of edges, wherein the pair of edge lines intersect at a feature point candidate.

26. The method of claim 25 further comprising the step of selecting a sequence of pixels in a direction different to the direction of one of said pair of edge lines according to intensity gradients between adjacent contrast regions.

27. The method of claim 26, wherein said sequence is selected at least two pixel units away from the feature point candidate.

28. The method of claim 27 further comprising the step of selecting a plurality of intensity values on each of said pair of edge lines contained in said sequence.

29. The method of claim 28 further comprising the step of fitting a curve equation to the intensity values for determining the location of each of said pair of edge lines to sub pixel accuracy.

30. The method of claim 29 further comprising the step of performing a linear regression on the intensity values of sub pixel accuracy for each said pair of edge lines.

31. The method of claim 30 further comprising the step of calculating the intersections of the edge lines resulting from the regression for determining the sub pixel location of the feature point candidate at an intensity saddle point.

32. The method of claim 29, wherein the curve fit is second order or higher.

33. A computer readable medium storing an algorithm for performing the method steps of claim 20.

34. The system according to claim 1 further comprising a second target pattern secured to the object, the second target pattern being movable within a predefined path in relation to the target pattern.

35. The system according to claim 34, wherein the relative position of the second target pattern along the path is determined in relation to the pose of the object.

36. The system according to claim 1, wherein the testing and comparing by the processor includes the relative orientation of the feature points with respect to one another.

37. The method according to claim 20, wherein the steps of testing and comparing includes the relative orientation of the feature points with respect to one another.

* * * * *